(12) United States Patent
Ogawa et al.

(10) Patent No.: US 9,814,847 B2
(45) Date of Patent: Nov. 14, 2017

(54) DRUG SOLUTION TANK AND DRUG SOLUTION PACK FOR ULTRASONIC INHALER

(71) Applicant: OMRON HEALTHCARE CO., LTD., Muko-shi, Kyoto (JP)

(72) Inventors: Hiroshi Ogawa, Kyoto (JP); Makoto Tabata, Kyoto (JP); Kenshin Tanaka, Kyoto (JP); Susumu Kutsuhara, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 412 days.

(21) Appl. No.: 14/724,293

(22) Filed: May 28, 2015

(65) Prior Publication Data
US 2015/0265786 A1  Sep. 24, 2015

Related U.S. Application Data

(63) Continuation of application No. PCT/JP2013/080982, filed on Nov. 18, 2013.

(30) Foreign Application Priority Data

Jan. 9, 2013  (JP) .................................. 2013-001455

(51) Int. Cl.
  *B05B 17/06* (2006.01)
  *A61M 15/00* (2006.01)
(52) U.S. Cl.
  CPC .... *A61M 15/0085* (2013.01); *A61M 15/0028* (2013.01); *A61M 15/0043* (2014.02); *A61M 15/0065* (2013.01); *A61M 2202/04* (2013.01)

(58) Field of Classification Search
  CPC .......... A61M 15/0061; A61M 15/0028; A61M 15/0043; A61M 15/0085; A61M 2202/04;
(Continued)

(56) References Cited

U.S. PATENT DOCUMENTS 3,561,444 A * 2/1971 Boucher ........... A61M 15/0085
                                              128/200.16
3,746,000 A   7/1973 Edwards
(Continued)

FOREIGN PATENT DOCUMENTS

JP    S5545335 U    9/1953
JP    4874090 B1    10/1973
(Continued)

OTHER PUBLICATIONS

Feb. 18, 2014 International Search Report issued in International Application No. PCT/JP2013/080982.

*Primary Examiner* — Joshua Lee
(74) *Attorney, Agent, or Firm* — Oliff PLC

(57) ABSTRACT

A drug solution tank of the present invention is a drug solution tank for an ultrasonic inhaler, including a drug solution reservoir portion having an upper edge that surrounds an opening and a bottom portion formed so as to protrude downward, a flange portion formed so as to extend outward from the upper edge of the drug solution reservoir portion, and a leg portion that is continuous with the outer perimeter or lower surface of the flange portion, is formed so as to surround the drug solution reservoir portion, and extends downward past the bottom portion of the drug solution reservoir portion.

9 Claims, 4 Drawing Sheets

(58) Field of Classification Search
CPC ...... B65D 43/06; B65D 43/065; B65D 43/08; B65D 51/002; B65D 51/28; B65D 51/2814; B65D 51/2821; B65D 51/2828; B65D 51/2835; B65D 51/2857
See application file for complete search history.

(56) References Cited

U.S. PATENT DOCUMENTS

| | | | | |
|---|---|---|---|---|
| 3,774,602 | A * | 11/1973 | Edwards | A61M 15/0085 128/200.16 |
| 4,428,384 | A * | 1/1984 | Raitto | A61B 10/007 600/573 |
| 5,361,989 | A * | 11/1994 | Merchat | A61M 11/005 239/102.2 |
| 5,865,171 | A * | 2/1999 | Cinquin | A61M 11/005 128/200.14 |
| 6,283,118 | B1 * | 9/2001 | Lu | A61M 11/005 128/200.16 |
| 7,261,102 | B2 * | 8/2007 | Barney | A61M 15/0028 128/200.14 |
| 2003/0052074 | A1 * | 3/2003 | Chang | B01L 3/50825 215/247 |
| 2006/0102172 | A1 * | 5/2006 | Feiner | A61M 15/0065 128/200.14 |
| 2009/0139951 | A1 * | 6/2009 | Chen | B65D 51/2835 215/227 |
| 2013/0092690 | A1 * | 4/2013 | Skakoon | B65D 51/2835 220/277 |
| 2014/0224815 | A1 * | 8/2014 | Gallem | A61M 15/0028 220/661 |

FOREIGN PATENT DOCUMENTS

JP H05123400 A 5/1993
JP 2012530562 A 12/2012

* cited by examiner

DRUG SOLUTION TANK AND DRUG SOLUTION PACK FOR ULTRASONIC INHALER

TECHNICAL FIELD

The present invention relates to a drug solution tank used by being mounted in an ultrasonic inhaler, and a drug solution pack including a drug solution tank and a drug solution sealed in the drug solution tank.

BACKGROUND ART

An inhaler (nebulizer) is used to atomize a drug solution for a patient to inhale for treatment of respiratory diseases such as asthma or a cold. In recent years, ultrasonic inhalers have been widely used, which are small in size and easy to use, even at home.

FIG. 8 schematically shows a cross-section of a drug solution atomizing portion of an ultrasonic inhaler. An ultrasonic inhaler 50 atomizes a drug solution 55 in a drug solution tank 54 by transmitting oscillation energy generated by an oscillator 51 to the drug solution tank 54 via working water 53 in a working water tank 52. The atomized drug solution is sent to a patient inhalation port (58) by blown air 57. The drug solution tank 54 is mounted in the working water tank 52 and subsequently fixed by being pressed by an upper cover 56. In order to efficiently transmit the oscillation to the internal drug solution 55, the bottom portion of the drug solution tank 54 is formed thinly, and in order to prevent a case in which drug solution remains, the drug solution tank 54 has a shape in which the central portion is more recessed near the oscillator (a shape that protrudes downward, such as a cone, pyramid, or shape in which only the central portion is recessed). For this reason, the drug solution tank 54 breaks and deforms easily and is exchanged as needed.

A user such as a patient, caregiver, or nurse inserts the drug solution into the drug solution tank each time of use and the drug solution is inhaled. At this time, there is a possibility that the user will use the wrong type or dosage of the drug solution. After inhalation ends, the user disposes of the drug solution and cleans the drug solution tank. However, problems regarding sanitation, such as contamination during insertion of the drug solution or during storage of the drug solution tank, have occurred in some cases due to repeated use of the drug solution tank.

Patent Literature 1 discloses a disposable single-shot ultrasonic atomizer. With this atomizer, a measured dosage amount of a liquid is sealed inside of a completely hermetically-sealed outer envelope (corresponds to a combination of the drug solution tank 54 and the upper cover 56 shown in FIG. 8), and the atomizer is used by being set in an ultrasonic energy supply machine. According to this, it is possible to prevent usage of the wrong dose of medicine and contamination at the time of insertion.

CITATION LIST

Patent Literature

Patent Literature 1: JP S48-074090A

SUMMARY OF INVENTION

Technical Problem

The atomizer disclosed in Patent Literature 1 is problematic in that it results in a large waste of resources since the entirety of the outer envelope is disposed of each time inhalation is performed. On the other hand, the conventional ultrasonic inhaler shown in FIG. 8 above is problematic in that the drug solution tank breaks and deforms easily during transport, storage, and the like, due to only the drug solution tank portion being made disposable.

The present invention has been made in consideration of the foregoing problems, and it is an objective thereof to provide a disposable drug solution pack that includes a drug solution tank and a drug solution sealed in the drug solution tank, and can be used by being mounted as-is in an ultrasonic inhaler, according to which it is possible to reduce the likelihood of the drug solution tank breaking or deforming during transport or storage. It is also an objective thereof to provide a drug solution tank that can be used in such a drug solution pack.

Solution to Problem

A drug solution tank for an ultrasonic inhaler of the present invention has a drug solution reservoir portion, a flange portion, and a leg portion. The drug solution reservoir portion has an upper edge that surrounds an opening, and a bottom portion that is formed so as to protrude downward. The flange portion is formed so as to extend outward from the upper edge of the drug solution reservoir portion. The leg portion is continuous with the outer perimeter or lower surface of the flange portion, is formed so as to surround the drug solution reservoir portion, and extends downward past the bottom portion of the drug solution reservoir portion.

Here, "up" and "down" refer to up and down in the case of holding the drug solution tank in an orientation in which the drug solution, which is in the drug solution reservoir portion, will not be spilled. The protrusion in the downward direction is a shape whose central portion is recessed, examples of which include a cone, a pyramid, a hemisphere, and a shape whose central portion alone is recessed. According to this kind of configuration, the bottom portion of the drug solution reservoir portion, which breaks and deforms easily, is protected by the foot portion, and therefore it is possible to reduce the likelihood of breakage and deformation during transport, storage, and the like.

Preferably, the leg portion is partitioned from the drug solution reservoir portion via a gap. Accordingly, it is possible to reliably fit the drug solution tank together with the inhaler body at a cross-sectionally U-shaped portion created by the drug solution reservoir portion, the flange portion, and the leg portion. Also, it is furthermore preferable that the dimension of the gap between the outer surface of the drug solution reservoir portion and the inner surface of the leg portion substantially matches the dimension of a working water tank in which the drug solution tank is to be mounted for transmitting oscillation energy of ultrasonic waves to the drug solution reservoir portion (Note that "substantially matching" means that a dimension tolerance set in the designs of the gap and the upper edge of the working water tank is allowed). Accordingly, it is possible to more accurately fit the upper edge of the working water tank into the gap.

Preferably, the leg portion is formed in a cylinder that continuously surrounds the periphery of the outer surface of the drug solution reservoir portion (note that "cylinder" includes tubes and square tubes). Accordingly, the entire perimeter of the drug solution reservoir portion, which breaks and deforms easily, is protected by the foot portion, and therefore it is possible to further reduce the likelihood of breakage or deformation of the drug solution tank during transport, storage, or the like.

More preferably, the shape of the cylinder of the leg portion conforms to the shape of the outer surface of the drug solution reservoir portion. Accordingly, the dimension of the gap between of the outer surface of the drug solution reservoir portion and the inner surface of the leg portion can be made substantially constant in the circumferential direction, and the gap does not expand in comparison to other regions at a specific region in the circumferential direction. Accordingly, it is possible to further reduce the likelihood of breakage and deformation of the drug solution tank during transport, storage, or the like.

Preferably, the leg portion extends further downward than the bottom portion of the drug solution reservoir portion does. According to this, the bottom portion of the drug solution reservoir portion, which breaks and deforms easily, is protected more reliably by the leg portion. Accordingly, it is possible to further reduce the likelihood of breakage and deformation of the drug solution tank during transport, storage, or the like.

Preferably, the drug solution tank is formed integrally using one sheet. According to this, the entirety of the drug solution tank can be made more difficult to break and deform.

Preferably, the flange portion has a horizontal portion that is continuous over the entire circumference of the upper surface thereof. According to this, in the case of manufacturing the drug solution pack by sealing the drug solution, it is possible to easily bond the lid member to the horizontal portion, and water-tightness can be more reliably obtained.

The drug solution pack for the ultrasonic inhaler of the present invention includes one of the above-described drug solution tanks, a lid member, and a drug solution. The lid member is bonded with the drug solution tank at the flange portion so as to close the opening such that it is water-tight. The drug solution is inserted into the drug solution reservoir, which is hermetically sealed by the lid member.

According to this kind of configuration, the drug solution pack can be used by being mounted as-is in an ultrasonic inhaler, and it is thereby possible to prevent a user from using the wrong type or amount of the drug solution, and it is possible to reduce the likelihood of contamination accompanying the task of inserting the drug solution into the drug solution tank. Also, by using one of the above-described drug solution tanks, the bottom portion of the drug solution reservoir portion, which breaks and deforms easily, is protected by the foot portion, and therefore it is possible to reduce the likelihood of the drug solution pack breaking or deforming during transport, storage, or the like.

Preferably, the sealed drug solution is a single-use amount. A single-use amount is an amount that is to be used by a patient in one instance of inhaling.

Advantageous Effects of Invention

As described above, according to the drug solution tank of the present invention, it is possible to reduce the likelihood of breakage or deformation during transport, storage, or the like. Also, according to the drug solution pack of the present embodiment, it is possible to reduce the likelihood that the drug solution tank will break or deform, even in the case of transport or storage in a state in which the drug solution is inserted in the drug solution tank in advance, and the drug solution pack can be used by being mounted as-is in an ultrasonic inhaler.

DESCRIPTION OF EMBODIMENTS

Figure 2:
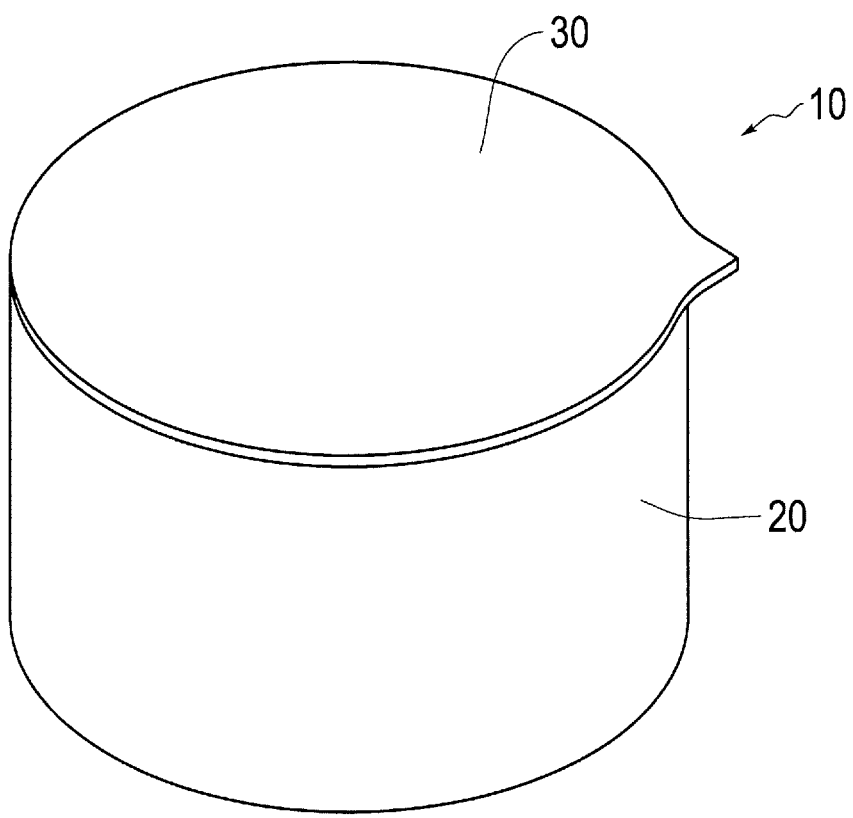
FIG. 2 is a perspective view of the exterior of a drug solution pack according to an embodiment of the present invention.
Figure 8:
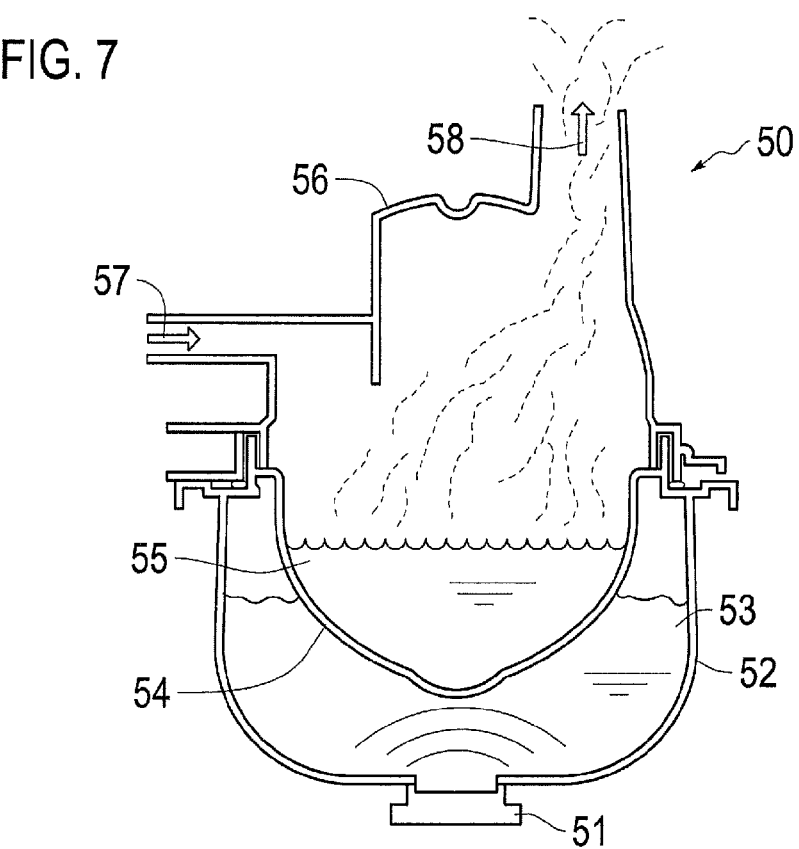
FIG. 8 is a cross-sectional view of an atomizing portion of a conventional ultrasonic inhaler.

An embodiment of a drug solution pack of the present invention will be described hereinafter with reference to the drawings. FIG. 2 shows the external appearance of a drug solution pack according to the present embodiment. FIG. 1 shows a cross-section of a drug solution pack according to the present embodiment. In FIG. 1, the drug solution pack 10 has a drug solution tank 20, a lid member 30, and a drug solution 40. The drug solution tank 20 has a flange portion 25, a leg portion 26, and a drug solution reservoir portion 21 that includes an upper edge 22 that surrounds an opening and a bottom portion 24 that is formed so as to protrude downward. The lid member 30 is in contact with the upper surface of the flange portion 25 and hermetically seals the opening of the drug solution reservoir portion 21. The drug solution 40 is sealed inside of the drug solution reservoir portion 21, which is hermetically sealed by the lid member 30.

In the drug solution tank 20 of the present embodiment, the drug solution reservoir portion 21 is composed of the upper edge 22 that surrounds the opening, a cylindrical middle portion 23 that is continuous below the upper edge 22, and a conical bottom portion 24 that is continuous below the middle portion 23 and is formed so as to protrude downward. In order to prevent a case in which the drug solution remains, the bottom portion 24 is formed into a shape whose central portion is more recessed near an oscillator, or in other words, is formed so as to protrude downward. The thickness of the drug solution tank is designed according to the material, the shape, and the oscillation strength. However, in order to efficiently transmit oscillation from the outside to the drug solution 40 on the inside, the bottom portion 24 is formed so as to be relatively thinner than the other portions.

The shape of the drug solution reservoir portion is not limited to that described above. For example, in another embodiment, the horizontal cross section need not be circular. Also, it is possible to not include a cylindrical middle portion that can clearly be distinguished from other portions, and the middle portion may be continuous with the bottom portion such that the radius gradually decreases starting from below the upper edge, as shown in FIG. 8. Also, instead of being conical, the bottom portion may be in another shape, such as a pyramid, or a hemisphere.

The flange portion 25 of the present embodiment is formed so as to extend outward from the upper edge 22 of the drug solution reservoir portion. Thus, due to the flange portion 25 being located in the uppermost portion of the drug solution tank 20, it is easy to hermetically seal the drug solution reservoir 21 by bonding the lid member 30. Also, it is preferable that a horizontal portion that is continuous over the entire circumference is formed on the upper surface of the flange portion 25. According to this, it is easier to bond the lid member 30.

The leg portion 26 of the present embodiment is continuous on the outer circumferential side on the lower surface of the flange 25, and is partitioned from the drug solution reservoir portion 21 via a gap 20a. In this example, dimension d of the gap 20a between the outer surface of the drug solution reservoir portion 21 and the inner surface of the leg portion 26 substantially matches the dimension of the upper edge of the working water tank (indicated by reference numeral 52 in later-described FIG. 3), on which the drug solution tank 20 is to be mounted. Accordingly, it is possible for the drug solution reservoir tank to fit together reliably with the inhaler body at a cross-sectionally U-shaped portion A (i.e., the portion surrounding the gap 20a) created by the drug solution reservoir portion 21, the flange portion 25, and the leg portion 26, without getting in the way of the lid member 30 being bonded to the upper surface of the flange portion 25.

Also, in this example, the leg portion 26 is formed in a cylindrical shape that continuously surrounds the perimeter of the outer surface of the drug solution reservoir portion 21. Accordingly, the entire perimeter of the drug solution reservoir portion 21, which breaks and deforms easily, is protected by the leg portion 26, and it is therefore possible to further reduce the likelihood of the drug solution tank 20 breaking or deforming during transport, storage, or the like. Moreover, in this example, the tubular shape (cylindrical shape) of the leg portion 26 conforms to the shape of the outer surface of the drug solution reservoir portion 21. Accordingly, the dimension of the gap 20a between of the outer surface of the drug solution reservoir portion 21 and the inner surface of the leg portion 26 can be made substantially constant in the circumferential direction, and no specific region of the gap 20a expands in proportion to other regions in the circumferential direction. Accordingly, it is possible to further reduce the likelihood that the drug solution 20 will break or deform during transport, storage, or the like.

Figure 3:
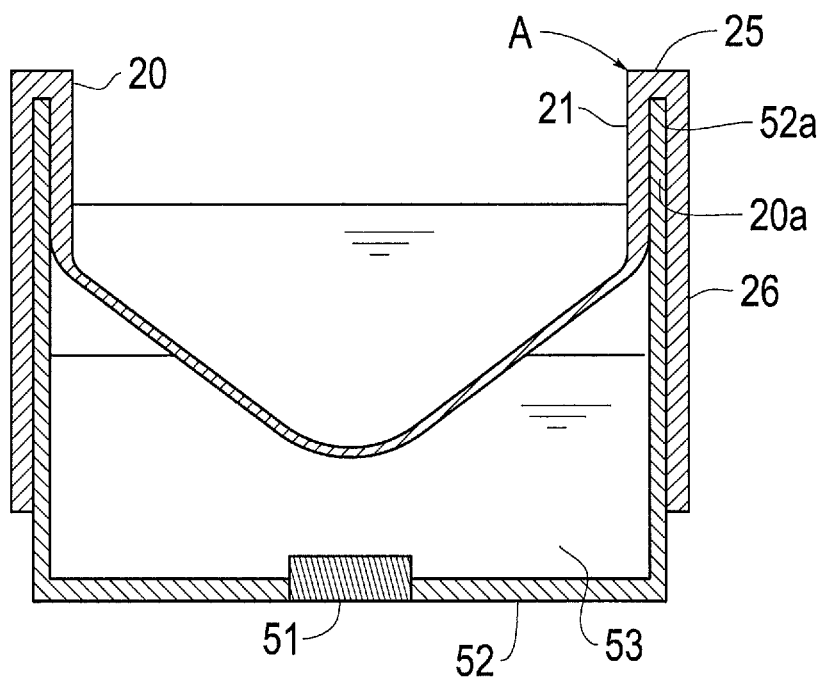
FIG. 3 is a diagram in which a drug solution tank according to an embodiment of the present invention is mounted in a working water tank.

FIG. 3 shows a cross-section in the case where the drug solution tank according to the present embodiment has been mounted in the working water tank. An oscillator 51 is present below the working water tank 52, and working water 53 has been inserted inside of the working water tank 52. The drug solution tank 20 fits on the upper edge 52a of the working water tank 52, at the cross-sectionally U-shaped portion A created by the drug solution reservoir portion 21, the flange portion 25, and the foot portion 26. The site on the ultrasonic inhaler body side on which the drug solution tank 20 is to be fit is not limited to being the upper edge of the working water tank, and by fitting the cross-sectionally U-shaped portion A on some site, it is possible to conveniently and reliably mount the drug solution tank on the inhaler body. In the mounted state, oscillation energy generated by the oscillator 51 is transmitted to the drug solution reservoir unit 21 via the working water 53 in the working water tank 52, whereby the drug solution in the drug solution reservoir portion 21 is atomized.

Figure 4:
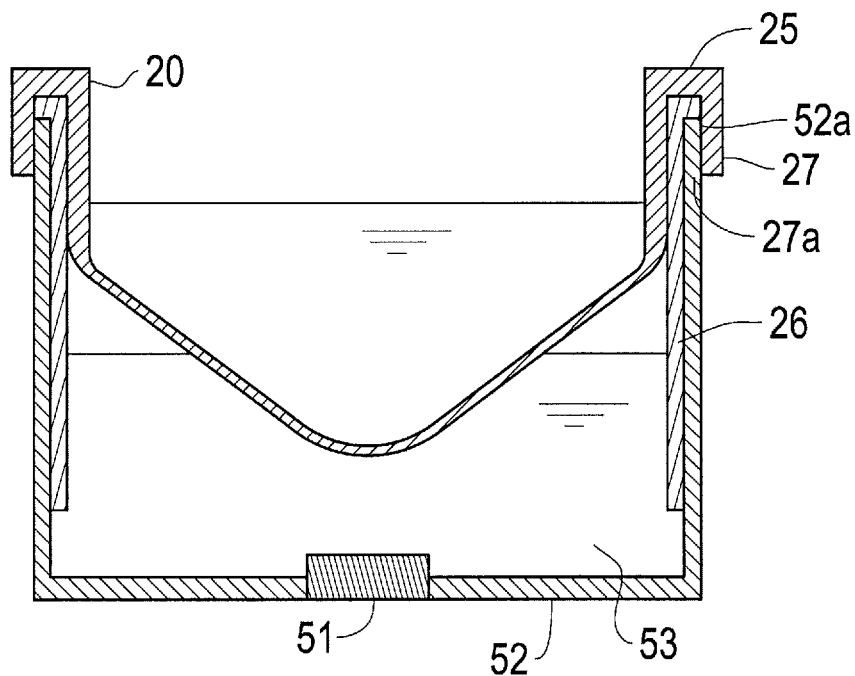
FIG. 4 is a diagram in which a drug solution tank according to an embodiment of the present invention is mounted in a working water tank.

Note that the drug solution tank can be fit on the upper edge or the like of the working water tank also in the case where no gap 20a is present between the leg portion and the drug solution reservoir portion. For example, in FIG. 4, a gap 27a between the leg portion 26 and a folded portion 27 in the outer perimeter of the flange portion is fit onto the upper edge 52a of the working water tank 52, and the leg portion 26 enters the working water tank 52. To compare FIGS. 3 and 4, FIG. 3 is preferable since the portions are fit together more reliably.

Figure 1:
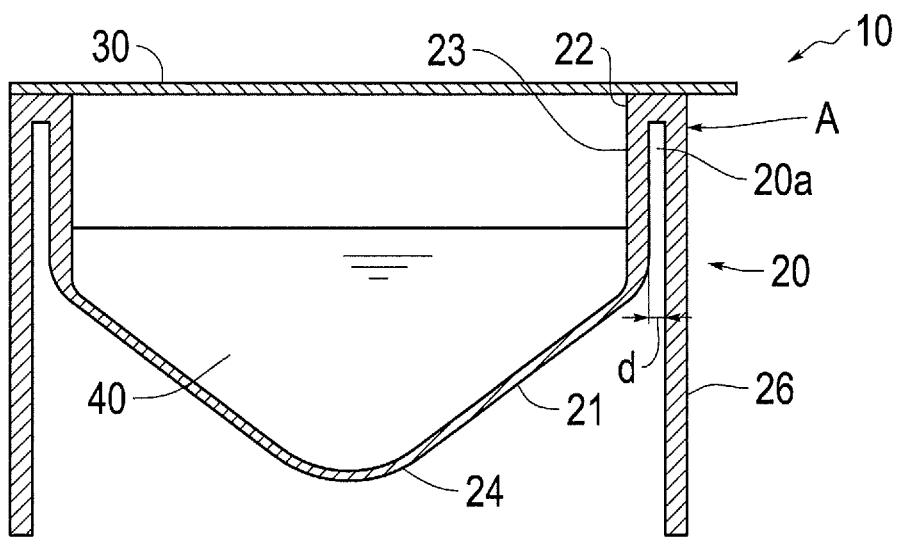
FIG. 1 is a cross-sectional view of a drug solution pack according to an embodiment of the present invention.

Also, in FIG. 1, the leg portion 26 of the present embodiment is formed so as to surround the drug solution reservoir portion 21, and extends downward past the bottom portion 24 of the drug solution reservoir portion. Accordingly, even when the drug solution pack is placed on a platform, for example, the bottom portion 24 of the drug solution reservoir portion does not come into direct contact with the platform. When the leg portion 26 is also formed so as to surround the drug solution reservoir portion 21, it is possible to reduce cases of coming into contact with the drug solution reservoir portion 21 from the outside, and to prevent the pointed shape of the bottom portion 24 of the drug solution reservoir portion from breaking or deforming.

The shape of the leg portion 26 is not limited to the description above. For example, even if the leg portion 26 is not formed so as to completely cover the drug solution reservoir portion 21, three or more legs appropriately arranged in a dispersed manner in the circumferential direction may be formed so as to surround the drug solution reservoir portion 21.

Figure 5:
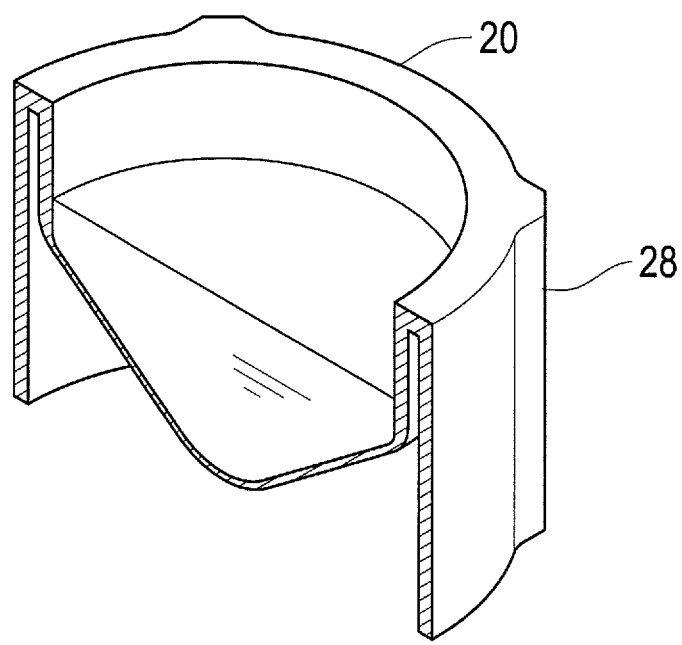
FIG. 5 is a cross-sectional perspective view of a drug solution tank according to an embodiment of the present invention.
Figure 6:
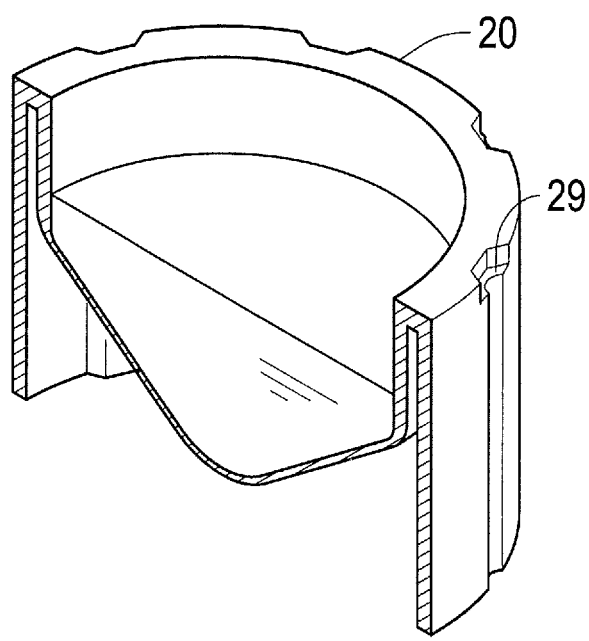
FIG. 6 is a cross-sectional perspective view of a drug solution tank according to an embodiment of the present invention.
Figure 7:
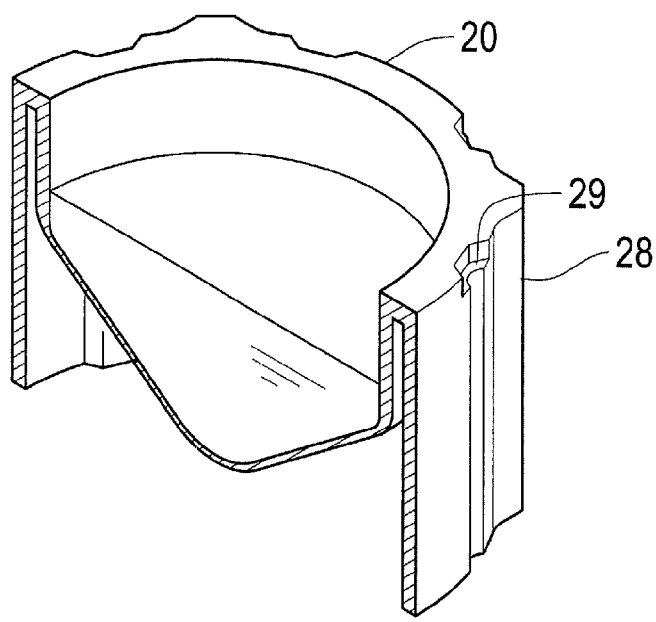
FIG. 7 is a cross-sectional perspective view of a drug solution tank according to an embodiment of the present invention.

Furthermore, in order to reinforce the strength, the leg portion 26 may be provided with ribs, and the connecting portion for the flange portion 25 and the leg portion 26 may be provided with a depression. FIG. 5 shows an example in which the leg portion 26 is provided with ribs 28, FIG. 6 shows an example in which the connecting portion for the flange portion 25 and the leg portion 26 is provided with depressions 29, and FIG. 7 shows an example in which both the ribs 28 and the depressions 29 are provided.

The material of the drug solution tank 20 is not particularly limited as long as it is resistant to the drug solution. For example, it is possible to use resin such as polypropylene, or the like. In this example, the drug solution tank 20 is formed integrally by vacuum molding one polypropylene sheet. Accordingly, the entirety of the drug solution 20 is made more difficult to break and deform.

The lid member 30 of the present invention is bonded to the upper surface of the drug solution tank flange portion 25 and closes the opening of the upper portion of drug solution reservoir portion such that it is water-tight and the drug solution inside does not leak out. The lid portion 30 can be formed of a variety of materials according to which resistance to the drug and formability of the film can be ensured, and for example, it is possible to use various types of resin film, foil of various types of metal such as aluminum, material obtained by laminating these materials, and the like. There is no particular limitation to the bonding method, as long as sanitation and ecological safety can be ensured. Note that the strength of bonding needs to be of such a degree that the lid member 30 can be pulled off and opened when used by a user.

Regarding the drug solution 40 of the present embodiment, an appropriate amount of an appropriate type of drug solution is inserted based on individual information such as the condition and age of the patient. Examples of drug solutions include inhalants used for treatment and prevention of asthma and other diseases. Also, the drug solution may be a normal saline solution or the like for prevention and care of colds. It is preferable that the amount of the drug solution is an amount that can be used completely in one instance of mounting. Here, "being used completely in one instance of mounting" does not necessarily require that the drug solution is used completely in one instance of inhaling. For example, in the case of atomizing and aspirating a normal saline solution using a personal inhaler for the purpose of humidification in order to prevent colds or perform care at a time of catching a cold, the drug solution inside of one drug solution pack may be inhaled over multiple instances. It is furthermore preferable that the amount of the drug solution is a single-use amount. In such a case, the drug solution can be completely used in one instance of inhaling, and it is possible to further reduce the likelihood that a problem regarding sanitation will occur. Also, since the amount of drug solution used varies depending on the condition, age, and the like of the patient as well, the amount of drug solution to be sealed may be changed according to the patient. For example, a drug solution needed for treatment of a patient may be sealed using only a single-use amount thereof corresponding to the condition, age, and the like of the patient.

Regarding the manufacturing method of the present drug solution pack 10, it can be manufactured by inserting the drug solution 40 into the drug solution tank 20, covering it with the lid member 30, and bonding the lid member 30 with the flange portion 25 of the drug solution tank using heat welding, or the like.

Next, a method for using the drug solution pack according to the present embodiment will be described. The drug solution pack of the present embodiment is manufactured at a factory, packaged as appropriate, and distributed. It has already been stated above that when the drug solution pack is transported or stored in the distributing stage, the configuration thereof prevents breakage and deformation of the pointed shape of the bottom portion 24 of the drug solution reservoir portion.

The user can use the drug solution pack of the present embodiment as described below. For example, the user unwraps the packaging of the drug solution pack, inserts tap water or the like as working water into the working water tank of the ultrasonic inhaler, and mounts the drug solution pack of the present embodiment therein. Next, the user pulls off the lid member with his or her fingers so as to unseal the pack and attaches an upper cover so as to assemble the inhaler. Then, the user performs inhalation. After inhalation, the upper cover is opened, the drug solution tank and remaining drug solution are disposed of, and the working water is thrown out.

REFERENCE SIGNS LIST

A Cross-sectionally U-shaped portion
10 Drug solution pack
20 Drug solution tank
20*a*, 27*a* Gap
21 Drug solution reservoir portion
22 Upper edge of drug solution reservoir portion
23 Middle portion of drug solution reservoir portion
24 Bottom portion of drug solution reservoir portion
25 Flange portion
26 Leg portion
27 Folded portion on outer perimeter of flange portion
28 Rib
29 Depression
30 Lid member
40 Drug solution
50 Ultrasonic inhaler
51 Oscillator
52 Working water tank
52*a* Upper edge of working water tank
53 Working water
54 Drug solution tank
55 Drug solution
56 Upper cover
57 Blown air
58 To patient inhalation port

The invention claimed is:

1. A drug solution tank for an ultrasonic inhaler, comprising:
- a drug solution reservoir portion having an upper edge that surrounds an opening and a bottom portion formed so as to protrude downward;
- a flange portion formed so as to extend outward from the upper edge of the drug solution reservoir portion; and
- a leg portion that is continuous with the outer perimeter or lower surface of the flange portion, is formed so as to surround the drug solution reservoir portion, and extends downward past the bottom portion of the drug solution reservoir portion.

2. The drug solution tank for an ultrasonic inhaler according to claim 1, wherein
- the leg portion is partitioned from the drug solution reservoir portion via a gap.

3. The drug solution tank for an ultrasonic inhaler according to claim 1, wherein
- the leg portion is formed in a cylinder that continuously surrounds the periphery of the outer surface of the drug solution reservoir portion.

4. The drug solution tank for an ultrasonic inhaler according to claim 3, wherein
- the shape of the cylinder of the leg portion conforms to the shape of the outer surface of the drug solution reservoir portion.

5. The drug solution tank for an ultrasonic inhaler according to claim 1, wherein
- the leg portion extends further downward than the bottom portion of the drug solution reservoir portion does.

6. The drug solution tank according to claim 1, wherein the drug solution tank is formed integrally using one sheet.

7. The drug solution tank according to claim 1, wherein the flange portion has a horizontal portion that is continuous over the entire circumference of the upper surface thereof.

8. A drug solution pack for an ultrasonic inhaler, comprising:
- the drug solution tank according to claim 1;
- a lid member that is bonded with the drug solution tank at the flange portion so as to close the opening such that it is water-tight; and
- a drug solution sealed inside of the drug solution reservoir portion, which is hermetically sealed by the lid member.

9. The drug solution pack according to claim 8, wherein the sealed drug solution is a single-use amount.

* * * * *